(12) United States Patent
Di Napoli

(10) Patent No.: US 6,844,365 B2
(45) Date of Patent: Jan. 18, 2005

(54) SUBSTANCES FOR USE IN TREATING PSORIASIS

(75) Inventor: Guido Di Napoli, Collonge-Bellerive (CH)

(73) Assignee: Laboratoire Medidom S.A., Geneva (CH)

(*) Notice: Subject to any disclaimer, the term of this patent is extended or adjusted under 35 U.S.C. 154(b) by 0 days.

(21) Appl. No.: 09/798,355

(22) Filed: Mar. 2, 2001

(65) Prior Publication Data

US 2002/0143057 A1 Oct. 3, 2002

Related U.S. Application Data

(63) Continuation of application No. PCT/IB01/00005, filed on Jan. 8, 2001.

(30) Foreign Application Priority Data

Jan. 12, 2000 (CH) .............................................. 0053/00

(51) Int. Cl.[7] ........................ A61K 31/19; A61K 31/235
(52) U.S. Cl. ........................................ 514/569; 514/533
(58) Field of Search ................................. 514/569, 533

(56) References Cited

U.S. PATENT DOCUMENTS 4,244,968 A    1/1981    Friedmann
4,346,103 A    8/1982    Friedmann

FOREIGN PATENT DOCUMENTS

| | | |
|---|---|---|
| EP | 0809995 A1 | 12/1997 |
| EP | 0822178 A1 | 2/1998 |
| EP | 0636602 B1 | 4/1998 |
| EP | 0822177 A1 | 12/1998 |
| EP | 0928781 A1 | 7/1999 |
| FR | 2508798 | 1/1983 |
| JP | 10129556 | 5/1995 |
| JP | 10114650 | 5/1998 |

OTHER PUBLICATIONS

Kelly et al., Textbook of Rheumatology, 4th ed., vol. 1., pp. 522–523; 974–984, W.B. Saunders Company, Philadelphia, PA 1993.

Budavari, et al., Merck Index, The., 12th ed., pp. 501–502, Merck Research Laboratories, Whitehouse Station, NJ 1996.

*Primary Examiner*—Rebecca Cook
(74) *Attorney, Agent, or Firm*—Fulbright & Jaworski L.L.P.

(57) ABSTRACT

It is disclosed the use of diacerein or a pharmaceutically acceptable derivative thereof for the manufacture of a pharmaceutical composition for the treatment of psoriasis or diseases associated therewith, such as psoriatic arthritis.

10 Claims, 9 Drawing Sheets

SUBSTANCES FOR USE IN TREATING PSORIASIS

The Application is a continuation of PCT/IB01/00005 filed on Jan. 8, 2001.

This invention relates to substances for use in treating psoriasis and diseases associated therewith.

Psoriasis is a heterogeneous, chronic inflammatory disease of the skin of unknown aetiology.

The prevalence of psoriasis in the world population is estimated at around 2 to 3% and varies from minimal lesions of the elbows and knees to a large number of lesions scattered over the skin, with men and women being equally affected.

Psoriasis may occur over any portion of the integument, such as the elbows, knees, scalp and nails.

In most patients, psoriasis vulgaris is mild to moderate in intensity and affects less than 20% of the skin.

Classical psoriasis appears as papules and plaques with layers of scales, the individual lesion being erythemateous covered with layer of silver white scale sharply demarcated from adjacent skin.

Psoriasis however occurs in a variety of patterns and may be associated with several forms of inflammatory arthritis, including asymetric oligoarthritis, symmetric arthritis, spondyloarthritis, and arthritis mutilans.

For example, psoriatic arthritis is estimated to occur in 2.7 to 7% of the general psoriatic population and in most cases, psoriatic arthritis appears several years after psoriasis.

Histologically, psoriasis is characterised by epidermal hyperproliferation/hyperplasia resulting from infiltration of inflammatory keratinoctes in the dermis, by increased vascularity and release of associated pro-inflammatory cytokines such as IL-1, IL-6, IL-8 and TNF-α.

The etiopathogenesis of psoriasis and its related arthritis (PsA) has not yet been comprehensively explained, but it is widely accepted that genetic, immunologic and environmental factors play important roles in the development and expression of these diseases.

The genetic role in the aetiology and pathogenesis of psoriasis and its related psoriatic arthritis is strongly supported by twin-studies of Espinoza L. R. in "Proceedings of the XIX ILAR Congress of Rheumatology 1997, Singapore, pp 262–263".

Research in the field also suggests the direct involvement of the immune system in the pathogenesis of psoriasis and its related psoriatic arthritis.

First of all, the presence of CD4+ and CD8+ lymphocytes in the skin and synovial membrane indicates that these cells participate in theses diseases.

Furthermore, evidence for the role of the immune system, particularly T cells, is provided by the effect of immunosuppressive agents in the inflammatory psoriatic process in both skin and synovium and several immunosuppressive agents, including methotrexate and cyclosporine A are very effective in controlling activity in psoriasis and its related psoriatic arthritis.

Furthermore, Espinoza has shown that psoriatic fibroblasts may contribute in a significant way to the inflammatory and proliferative changes observed in psoriasis and its related psoriatic arthritis.

Psoriatic fibroplasts in both skin and synovium exhibit alterations in DNA cell-cycle and growth factor responses, cause an increase in the expression of platelet derived growth factor (PDGF)-β receptor and in the production of interleukin IL-1β, interleukin-8 (IL-8) and PDGF, and further constitutively express interleukin-6 (IL-6).

This indicates that IL-1β, IL-6 and IL-8 which are pro-inflammatory cytokines, are expressed in psoriasis and its related psoriatic arthritis.

Further, in the synovial fluid of patients suffering from psoriasis and related arthritis, high levels of tumour necrose factor (TNF-α), IL-1, IL-6 and IL-8 have been found.

The currently available treatments modalities for psoriasis can be divided into three main categories: topical, photo and systemic therapies (cyclosporine, methotrexate, oral retinoids).

A large number of pharmaceutical compositions used in the treatment of psoriasis are reported with varying degrees of success and are often accompanied by undesired side effects.

Furthermore, currently available treatments for psoriasis are not capable of curing the disease and the goal of these treatments is only to decrease the severity and extent of the cutaneous lesions.

Until the present invention, there has been no effective therapeutic treatment of psoriasis or psoriasis and associated conditions such as psoriatic arthritis.

Considering the potential seriousness of psoriasis and related diseases and the relatively high prevalence in the general population, and further considering that psoriasis has been reported and studied since the early nineteenth century, there is a significant long-felt need for an effective therapeutic treatment of psoriasis and diseases associated herewith.

The object of the present invention is thus to provide a substance for use in treating psoriasis and diseases associated therewith.

According to the present invention, this object has been achieved as a result of the inexpected findings that diacerein can be useful in the treatment of psoriasis and diseases associated therewith.

Diacerein, also named diacerhein, diacetylrhein or 4,5-bis(acetyloxy)-9,10-dihydro-9,10-dioxo-2-anthracene carboxylic acid (see The Merck Index, Twelfth Edition, 1996, Product No. 3003, pages 501–502), is an anthraquinone derivative with the following structure:

and is known for its use in the treatment of rheumatoid arthritis and osteoarthritis, for example as described in U.S. Pat. No. 4,244,968 (Prof. C. A. FRIEDMANN), EP-B-0 520 414 (MADAUS AG) and EP-B-0 636 602 (LABORATOIRE MEDIDOM S.A.).

Various formulations for parenteral or oral administration of diacerein derivatives have been proposed.

An advantageous preparation for oral administration is for example described in EP-A-0 264 989.

Whereas diacerein and its derivatives have been considered for the treatment of rheumatoid arthritis and osteoarthritis, both seropositive to rheumatoid factor, they have not, prior to the present invention, been considered for the treatment of psoriasis and associated conditions such as psoriatic arthritis seronegative to the rheumatoid factor.

The mechanism of diacerein and rhein derivatives in the treatment of psoriasis and its related arthritis (PsA) is not entirely clear, however diacerein and its active metabolite rhein have been shown to inhibit the synthesis and activity of pro-inflammatory catabolic cytokines of the IL-1 family, especially IL-1β, and the IL-1 receptor antagonist (IL-1ra) and have also been shown to inhibit IL-6 and other cytokines such as TNF-α and LIF.

It is thus assumed that the aforementioned effects of diacerein on cytokines is one of a possible reason for its effectiveness in the treatment of psoriasis since there is an expression of high levels of TNF-α, IL-1, IL-6 and IL-8 in the synovial fluid of patients sufferiing from psoriasis and psoriatic arthritis.

According to one aspect, the present invention concerns the use of diacerein or a pharmaceutically derivative thereof or rhein for the manufacture of a pharmaceutical composition for the treatment of psoriasis and diseases associated therewith.

According to another aspect, the present invention concerns the use of diacerein or a pharmaceutically acceptable derivative thereof or rhein for the manufacture of a pharmaceutical composition for the treatment of psoriasis.

According to still another aspect, the present invention concerns the use of diacerein or a pharmaceutically acceptable derivative thereof or rhein for the manufacture of a pharmaceutical composition for the treatment of psoriasis and psoriatic arthritis.

According to still another aspect, the present invention concerns the use of diacerein for the manufacture of a pharmaceutical composition for the treatment of psoriasis.

According to still another aspect, the present invention concerns the use of diacerein for the manufacture of a pharmaceutical composition for the treatment of psoriasis and psoriatic arthritis.

According to still another aspect, the present invention concerns a method of treating psoriasis including administering a pharmaceutical composition comprising an effective amount of diacerein or a pharmaceutically acceptable derivative thereof or rhein.

According to still another aspect, the present invention concerns a method of treating psoriasis and psoriatic arthritis including administering a pharmaceutical composition comprising an effective amount of diacerein or a pharmaceutically acceptable derivative thereof or rhein.

The present invention satisfies a long-felt need by providing a particularly effective treatment of psoriasis and associated diseases by the use of diacerein or a pharmaceutically acceptable derivative thereof or rhein.

An advantage of the use of diacerein is that, as diacerein has already been extensively used for the treatment of osteoarthritis and rheumatoid arthritis, and has been subject of extensive toxicology studies, it is known to be well tolerated and does not show carcinogenic potential.

An other advantage of the diacerein is that has been shown not to effect prostaglandin PGE2 production and therefore does not have gastrotoxic potential.

Other advantages of the present invention will appear in the following detailed description.

Diacerein which can be used in the present invention may be any diacerein having a purity sufficient to be used in a pharmaceutical composition.

According to the Merck Index, Twelfth Edition, diacerein may be synthetized according to A. Tschirch, K. Heuberger, *Arch. Pharm.* 240, 596 (1902); V. K. Murty et al., *Tetrahedron* 23, 515 (1967).

Known formulations containing diacerein are for example Artrodar®, Art50®, Zondar50®, Fisiodar®, Artrofast®, Verboril®, Matrix®, Cartivix® and Artrolyt® (commercialized in FRANCE, ITALY, GREECE, PORTUGAL, ISRAEL, BRAZIL, ARGENTINA and PERU by LABORATOIRE MEDIDOM S. A (Geneva) or by its licensees, these formulations being commercialized to treat osteoarthritis.

Several processes for the preparation through extraction or synthesis of diacerein having a high pharmaceutical purity are protected by patents or patent applications held by or licensed to LABORATOIRE MEDIDOM S. A. (Geneva) (see for example EP-B-0 636 602, and EP-B-0 520 414).

A pharmaceutically acceptable derivative of diacerein which can be used in the present invention may be any derivative of diacerein pharmaceutically acceptable wherein the acid group of diacerein is in the form of a salt or of an ester.

Non-limiting examples of diacerein derivatives which can be used in the present invention are salts of alkali or alkali-earth metals such as sodium salt, potassium salt, magnesium salt, calcium salt, etc., and ester derived from $C_1$–$C_6$ alcohols such as ester derived from methanol, ethanol, etc.

However, use of diacerein is prefered.

In the present invention, the diacerein is preferably used to prepare pharmaceutical composition in a form acceptable for oral administration.

Pharmaceutical composition which are in a form acceptable for oral administration are for example syrups, tablets, capsules, etc.

When the pharmaceutical composition is in a form acceptable for oral administration, the dosage is preferably in the range from 30–200 mg daily, and more preferably 100 mg, daily.

The daily dosage is preferably administrated in at least two times.

A particularly effective dosage of diacerein in oral administration for the treatment of psoriasis is 100 mg twice daily for at least six months.

A pharmaceutical composition comprising diacerein or pharmaceutically acceptable derivatives thereof of rhein may also be provided in the form of a cream or ointment for topical application on the portions of integument affected by psoriasis, such as hyperkeratotic plaques.

When the pharmaceutical composition is in a form acceptable for topical administration, the dosage of the composition and the number of application daily are conveniently chosen to be effective.

The pharmaceutical compositions comprising diacerein or pharmaceutically acceptable derivatives thereof or rhein may be prepared by simple mixing of the diacerein or pharmaceutically derivative thereof or rhein with conventional appropriate excipients and making the composition in the appropriate galenic form or by any appropriate conventional method.

To illustrate the effect of the present invention, the present invention will now be described in details with reference to examples including in vitro tests, and clinical trials, and Figures.

EXAMPLES

In-vitro Evaluation of the Effect of Diacerein on Keratinocyte Proliferation and Measurements of the Release from Keratinocytes of the Main Cytokines Upon Diacerein Treatment Material and Methods In the present tests, pure diacerein was used.

Keratinocyte Cultures

Human epidermal keratinocytes were obtained from foreskin by dispase II (5 mg/ml for 60 minutes at 37° C., Boehringer Mannheim, Germany) separation of epidermal sheets.

The epidermis was incubated in 0.25% trypsin/0.02% EDTA for 20 minutes a 37° C. and mechanically disaggregated.

The epidermal cell suspensions were plated ($2.5 \times 10^4$/cm$^2$) on mytomicin C-treated 3T3-J2 cells ($2.4 \times 10^4$/cm$^2$), ATCC, Rockville, Md., USA) and cultured in 5% $CO_2$ humidified atmosphere in the keratinocyte growth medium: Dulbecco's modified Eagle's medium and Ham's F12 media (3:1 mixture, Biochrom KG, Berlin, Germany) containing fetal calf serum (10%, ICN Biomedicals, Aurora, Ohio), insulin (5 mg/ml, Sigma, St.Louis, Mo., USA), transferrin (5 mg/ml, Sigma), adenine (0.18 mM, Sigma), hydrocortisone (0.4 mg/ml, Sigma), triiodothyronine (20 pM, Sigma), cholera toxin (0.1 nM, Sigma), epidermal growth factor (10 ng/ml, Sigma), 4 mM glutamine (Sigma), and penicillin/streptomycin (50 IU/ml, Biochrom.).

In subconfluent primary cultures residual 3T3-J2 were detached with 0.02% EDTA and keratinocytes were trypsinized with 0.05% trypsin/0.02% EDTA and replated at a density of $5 \times 10^3$ cells/cm$^2$ on 3T3-J2 cells ($2.4 \times 10^4$/cm$^2$) mytomicin C-treated.

Subconfluent secondary cultures were trypsinized as above and replated for the experiments in defined serum-free medium (KGM, Clonetics Corp., Sans Diego, Calif., USA).

Cell viability was evaluated by trypan blue exclusion.

UV-B Radiation

UV-B radiation was delivered with a battery of lamps (TL 20W/12RS UV-B Philips Medical) before and after treatment with diacerein.

In other experiments, UVB irradiation was delivered only after diacerein addition.

Before irradiation, the cells were washed once with PBS and irradiated in presence of PBS.

Controls were sham irradiated for identical periods as measured by International Light Research Radiometer (Newburyport, Mass.).

Cell Proliferation Assay

Normal human keratinocytes (9000 cells/well) were grown on 96-well plates in KGM. and pretreated with diacerein or diluent alone.

Cells were counted at 24, 48 and 96 hours. In addition, $^3$H-thymidine (1 µCi/well, Amersham-Pharmacia Biotech, Rainham, UK) incorporation was performed 12 h before harvesting of the cells and cells were collected at 24, 48, 72 and 96 hours.

The incorporated radioactivity was determined by β-counter.

ELISA Assays

Quantitation of cytokine levels was performed by a quantitative two-site enzyme immunoassay according to manufacturer's instructions, using ELISA kits for IL-1, IL-6, IL-8 and TNF-α.

The sample concentration was determined by absorbance at 450 nm with the correction wavelength set at 540 nm.

RESULTS AND DISCUSSION

1. Viability of Keratinocytes by Trypan Blue Exclusion

In order to understand the effects of diacerein on human keratinocytes, a possible alteration of vital parameters was evaluated by the trypan blue exclusion.

Figure 1:
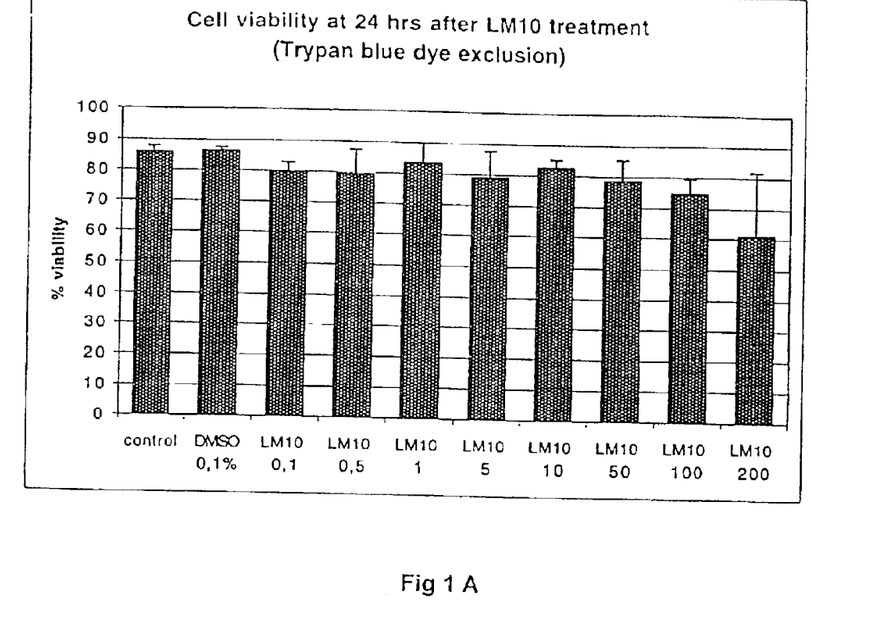
FIG. 1A represents a diagram showing the viability of keratinocytes at 24 hours after an in vitro diacerein treatment, measured by the trypan blue dye exclusion method.
FIG. 1B represents a diagram showing the viability of keratinocytes at 96 hours after an in vitro diacerein treatment measured by trypan blue dye exclusion method.

As shown in FIG. 1A and FIG. 1B, increasing doses of diacerein did not cause any significant alteration of keratinocyte viability except for the doses of 100 and 200 µM at 96 hours.

Thus, it is shown that diacerein does not affect keratinocyte vital parameters.

2. Keratinocyte Proliferation Assay

In order to evaluate the therapeutical effect of diacerein in psoriasis, cultured keratinocytes were provided increasing doses of the drug and keratinocytes were counted.

Figure 2:
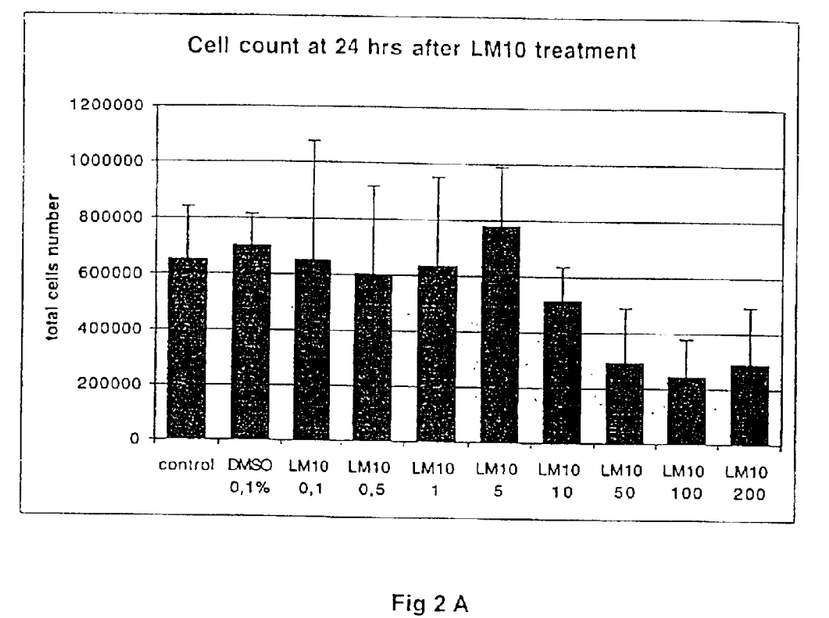
FIG. 2A represents a diagram showing keratinocyte count at 24 hours after an in vitro diacerein treatment.
FIG. 2B represents a diagram showing keratinocyte count at 96 hours after an in vitro diacerein treatment.
Figure 3:
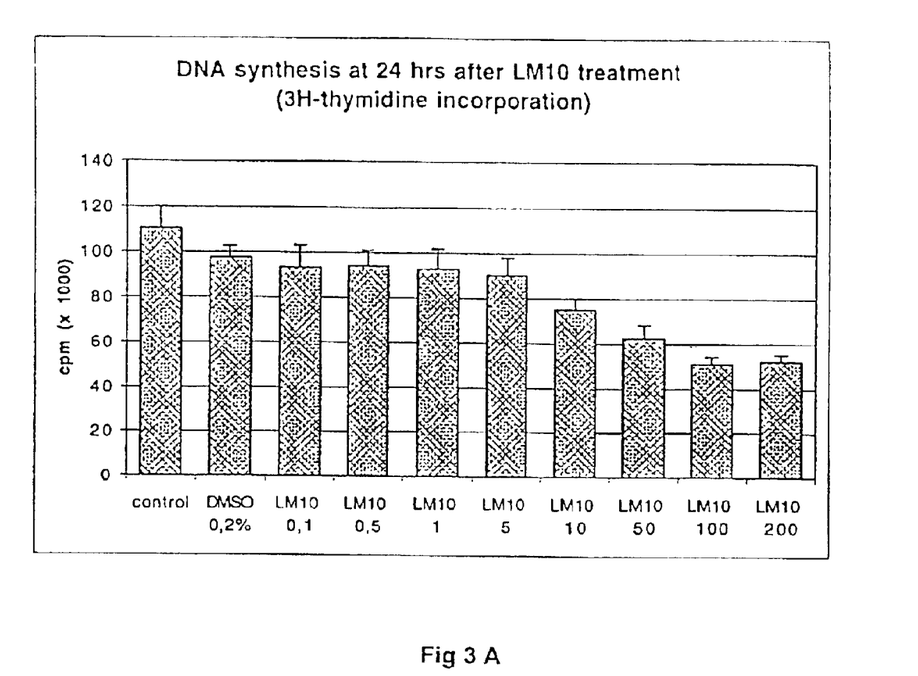
FIG. 3A represents a diagram showing DNA synthesis (3H-thymidine incorporation) at 24 hours after an in vitro diacerein treatment.
FIG. 3B represents a diagram showing DNA synthesis at 46 hours after an in vitro diacerein treatment (3H-thymidine incorporation).
FIG. 3C represents a diagram showing DNA synthesis at 72 hours after an in vitro diacerein treatment (3H-thymidine incorporation).
FIG. 3D represents a diagram showing DNA synthesis at 96 hours after an in vitro diacerein treatment (3H-thymidine incorporation).

As shown in FIG. 2A, cell number was significantly decreased 24 hours after treatment only when doses between 10 and 200 µM were used ($p < 0.05$).

On the other hand, as shown in FIG. 2B, at 96 hours after treatment, a clear dose-dependent decrease in keratinocyte number was observed starting with 5 of diacerein up to 100 µM ($p < 0.05$) (FIG. 2A and B).

This finding was confirmed by the striking effect of diacerein on DNA synthesis.

In particular, 3H thymidine incorporation was significantly and dose-dependently reduced by the addition of diacerein at 24 (10 to 200 µM), 48 ((1 to 200 µM), 72 and 96 (0.1 to 200 µM) hours after treatment (FIGS. 3A, 3B, 3C and 3D).

Taken together, these data point to diacerein as a potent inhibitor of keratinocyte proliferation.

3. IL-1 release by ELISA assay

IL-1 is constitutively expressed in human keratinocytes. IL-1 release was measured after the addition of increasing doses of diacerein.

Figure 4:
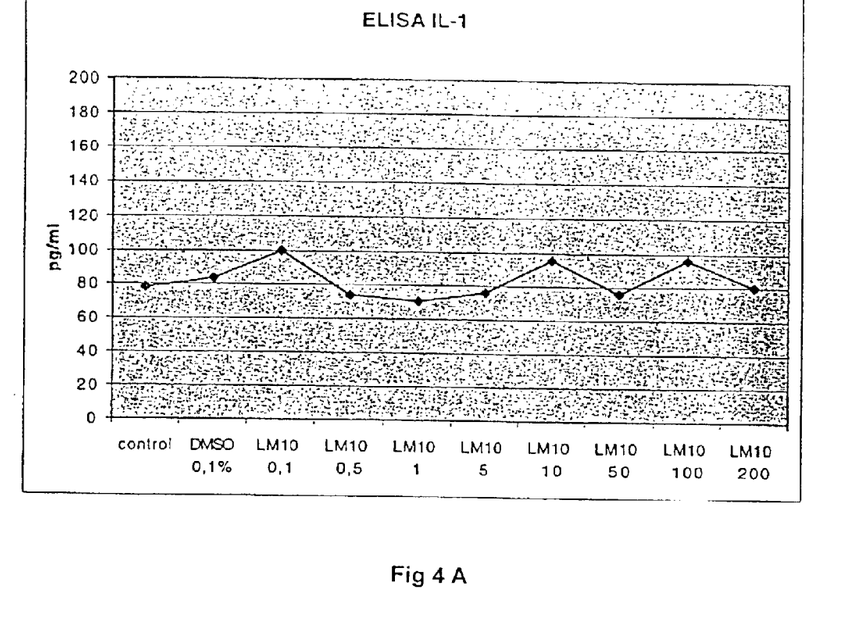
FIG. 4A represents a graphic showing IL-1 content by ELISA method.
FIG. 4B represents a graphic showing IL-1 content by ELISA method at 24 hours after UVB irradiation.

As shown in FIG. 4A, under normal conditions, diacerein did not affect the constitutive levels of IL-1 in keratinocytes Because it is known that UV light is the most potent stimulus for cytokine release, keratinocytes were UVB irradiated either before or after diacerein treatment.

As shown in FIG. 4B, while UVB cause d a tremendous increase in IL-1 release, diacerein prevented this effect 24 hours after irradiation.

In particular, as shown in FIG. 4B, diacerein turned out to be more powerful when administered before UVB irradiation.

It is pointed out that as little as 0.1 µM of the drug was capable of down-regulating IL-1 release almost to the baseline levels.

4. IL-6 Release by ELISA Assay

No constitutive levels of IL-6 are normally detected in human keratinocytes.

Therefore, IL-6 release was stimulated by UVB irradiation.

While diacerein did not affect IL-6 levels under basic conditions (FIG. 5A), it caused a reduction of UVB-induced IL-6 release at 24 hours after irradiation.

Diacerein was significantly more effective when added both before and after UVB light.

Figure 5:
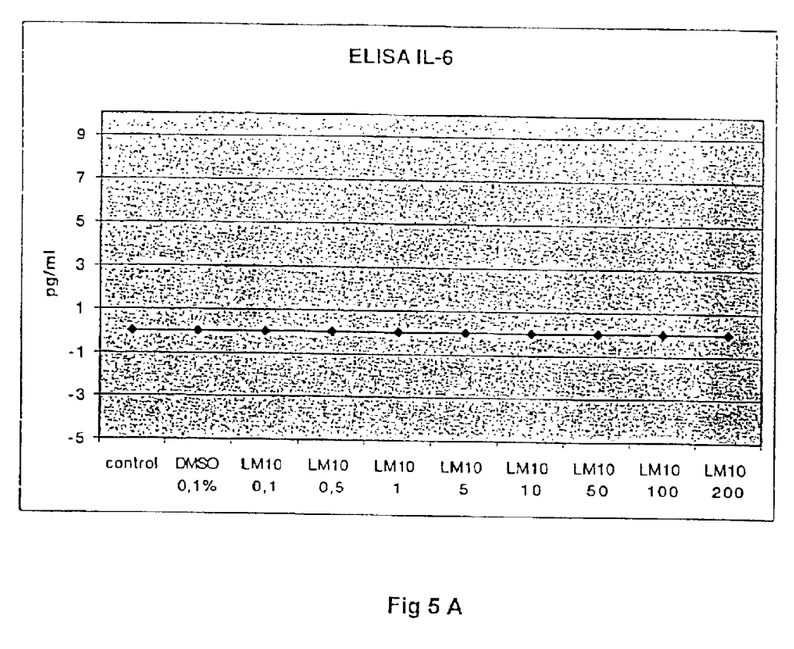
FIG. 5A represents a graphic showing IL-6 content by ELISA method.
FIG. 5B represents a graphic showing IL-6 content by ELISA method at 24 hours after UVB irradiation.

Indeed, in this case, a significant reduction in IL-6 release was observed with a dose of 1 µM, whereas 5 µM diacerein were necessary for a down regulation of IL-6 when the drug was administered only before UVB (FIG. 5B).

5. IL-8 Release by ELISA Assay

Figure 6:
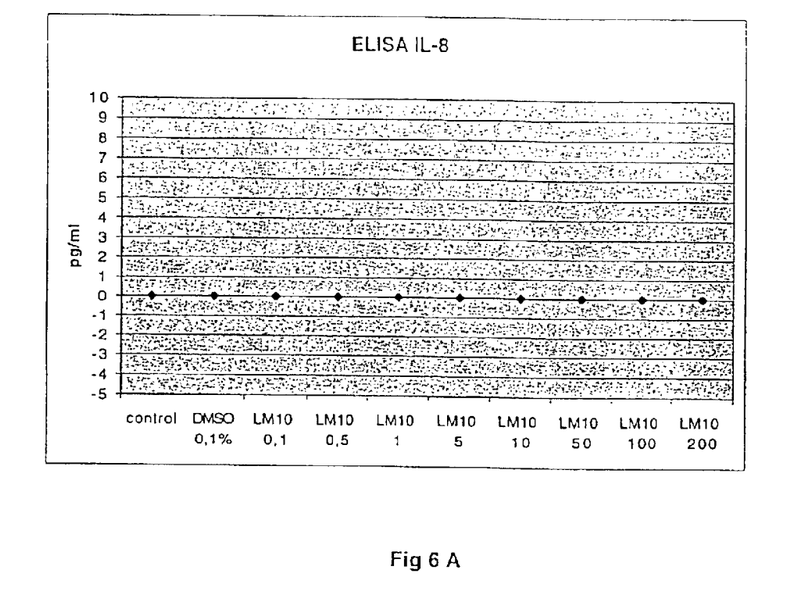
FIG. 6A represents a graphic showing IL-8 content by ELISA method.
FIG. 6B represents a graphic showing IL-8 content by ELISA method at 24 hours after UVB irradiation.
FIG. 6C represents a graphic showing IL-8 content by ELISA method at 24 hours after TNF-α treatment.

Similarly to IL-6, IL-8 was unaffected by diacerein under normal conditions (FIG. 6A).

However, when IL-8 release was up-regulated by UVB irradiation, diacerein (5–100 µM) caused a significant reduction of the cytokine levels at 24 hours.

Also in this instance, diacerein was more effective when given both before and after UVB irradiation (FIG. 6b).

As TNF-α is a potent inducer of IL-8 in keratinocytes and plays an important role in the pathogenesis of psoriasis, the effect of diacerein on IL-8 was also evaluated after stimulating keratinocytes with TNF-α.

Only high doses of diacerein (50–200 µM) were able to down-regulate TNF-α-induced IL-8 release in keratinocytes (FIG. 6C).

6. TNF-α Release by ELISA Assay

As mentioned above, TNF-α is of great relevance in the pathomechanisms of psoriasis. Therefore, we wanted to evaluate the effect of diacerein on the release of this cytokine from human keratinocytes.

Figure 7:
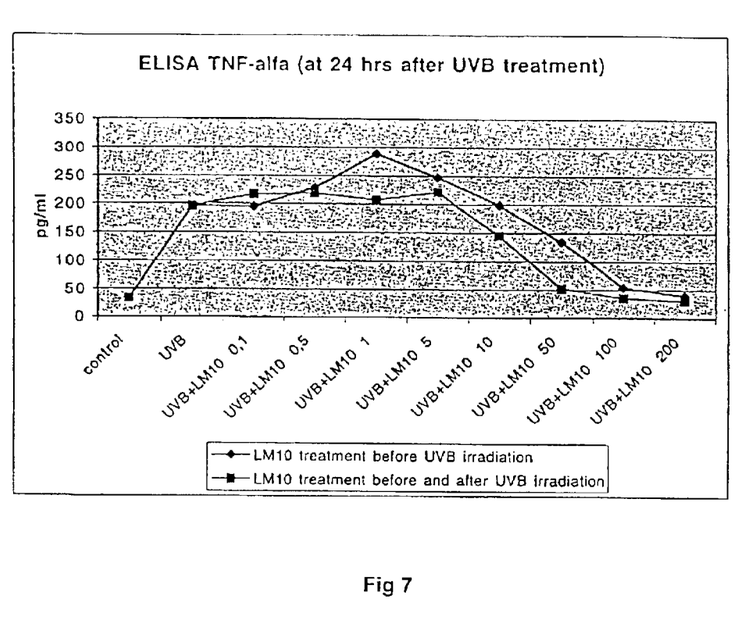
FIG. 7 represents a graphic showing TNF-α content by ELISA method at 24 hours after UVB irradiation.

Diacerein down-regulated UVB-induced TNF-α release only at high doses (50–200 µM) (FIG. 7).

The above in-vitro tests show clearly that diacerein can act on the two most important pathogenetic factors leading to the development of the psoriatic lesions, that is keratinocyte proliferation and alteration of the cytokine network.

These tests have shown that therapeutic levels of diacerein potently inhibited keratinocyte proliferation in a dose dependent manner and in addition that as little as 0.1 µM diacerein down regulated IL-1 release to almost baseline levels.

These tests have further shown that diacerein significantly down regulated UVB-induced release of IL-6, IL-8 and TNF-α, all of which are involved in the pathomechanisms of psoriasis.

Clinical Trials Showing the Efficacy and Safety of a Pharmaceutical Composition Containing Diacerein in the Treatment of Psoriasis and Psoriatic Arthritis The aim of this study was to assess the efficacy and safety of diacerein in the treatment of psoriasis with mild to moderate psoratic arthritis.

Pharmaceutical Composition to be Tested

The investigational drug, Artrodar® (Laboratoire Medidom S. A. (Geneva)), is a size 1 hard gelatin capsule.

The unit formula contained in each capsule is as follows:

| | |
|---|---|
| Diacerein | 50.0 mg |
| Lactose monohydrate | 214.5 mg |
| Croscarmellose sodium | 11.5 mg |
| Polyvidone K30 | 11.5 mg |
| Colloidal silicon dioxide | 11.5 mg |
| Magnesium stearate | 1.2 mg |

The capsule shell is as follows:

| | |
|---|---|
| Body: opaque white (002) | |
| Titanium dioxide | 2,3041 mg |
| Cap: opaque dark green (819) | |
| FD & C blue No. 2 | 0,4106 mg |
| Yellow iron oxide | 0,0272 mg |
| Titanium dioxide | 0,5434 mg |

Tested Patients

Ten patients satisfying all the inclusion and exclusion criteria indicated below were tested.

Inclusion criteria:

Male or female patients over 18 years of age with cutaneous involvement defined by the psoriasis area and severity index (PASI) (<15);

persistent negative latex test or ELISA for rheumatoid factors;

established diagnosis of mild to moderate severity psoriatic arthritis of at least 3 months duration characterized by oligoarthritis (<4 involved joints) and/or spondyloarthritis;

normal values for haematology and clinical chemistry values (ESR 1 h<30 mm, WBC with leucocyte differential count, RBC, Hb (>11 mg/dl), platelets, creatinine, transaminases, alkaline phosphatase, bilirubin);

normal or drug-controlled blood pressure values;

failure to respond to topical (including emollients and coal tar) and phototherapy;

evidence of medically approved contraceptive methods in women of childbearing age;

written informed consent from each patient;

Exclusion criteria:

patient under 18 years of age;

positive rheumatoid factor (RF) or antinuclear antibodies (ANA) >1:80;

history of inflammatory bowel disease or evidence of another rheumatologic disorder;

ascertained individual sensitivity to diacerein or any of the components in the capsule;

chronic illness that, in the opinion of the Investigator, would limit successful participation in the trial;

treatment with slow acting drugs and/or corticosteroids during the month prior to study start;

patient who, in the judgement of the Investigator, will comply with the protocol.

Treatment

Treatment was 2×50 mg capsules of Artrodar® (each capsule contains 50 mg diacerein) taken orally per day for 6 months.

One capsule was to be taken in the afternoon after lunch while the other was to be taken in the evening after dinner.

Concomitant Medication

No slow acting disease modifying drugs for psoriatic arthritis or corticosteroids were allowed during one month prior to the start of the study and throughout the study.

Treatment with NSAIDs, analgesics and other drugs was kept constant during the study and the doses used were recorded every week.

Efficacy Criteria

The following were assessed at baseline and at regular intervals during the study:

The PASI index (Fredriksson and Petterson, 1978)[i] for assessing cutaneous involvement.

Pain on activity (target joint) assessed using the VAS.

Ritchie articular index.

A patient was considered to be a treatment responder if she or he had an improvement in the severity of the psoriasis on the PASI score.

Safety Criteria

All adverse events either observed by the Investigator or reported by the doctor were recorded.

Results According to Summary Data of Table 1 and Individual Data of Table 2

A total of 10 patients with mild to moderate psoriatic arthritis were included into the study.

Three patients have completed baseline visit—no efficacy data available at the time this report was written.

One patient has taken the drug for 1 month.

Six patients have taken the drug for more than 1 month

Hence data are available for the 7 patients that took the drug for at least 1 month are presented in Table 1 (SUMMARY DATA). The raw data for each patient are enclosed in Table 2 (INDIVIDUAL DATA).

Of the 7 patients that took diacerein for more than 1 month, all responded to treatment as far as the psoriasis component is concerned (reduction in the PASI score).

4 patients responded after 1 month 2 patients responded after 2 months 1 patient responded after 3 months One of these patients dropped out of the study after 1 month of treatment due to diarrhea. However, both psoriasis and arthritis symptoms improved greatly during the 1-month treatment and therefore patient can be considered as a responder.

Of the remaining 3 patients, one did not show any improvement in the status of psoriasis as the patient had only completed 1 month of treatment whereas the remaining two patients only had their baseline visits completed.

TABLE 1

SUMMARY DATA

| Patient initials | Sex | Date of birth | Age (years) | Diagnosis | Duration of psoriasis | Results | Responder |
|---|---|---|---|---|---|---|---|
| M P | M | May 24, 1952 | 47 | Psoriatic arthritis | unknown | After 3 months treatment with Diacerein, psoriasis decreased significantly in extent and severity. Psoriasis improved further. After 4 months of treatment, slight psoriasis (erythema = slight) was found on the anterior part of scalp. Slight erythema and moderate desquamation observed on posterior part of scalp. It practically disappeared from the knee and left elbow. After 5 months of treatment, slight psoriasis was present on the anterior part of scalp (erythema = slight). The posterior part of the scalp showed slight erythema and desquamation. Left elbow showed only slight infiltration. No adverse events observed. | Yes |
| E M | M | Feb. 26, 1959 | 41 | Psoriatic arthritis | 21 years | After 2 months treatment with Diacerein, the psoriasis disappeared. About 1 month later, psoriasis re-appeared on the lower limbs and scalp (with a lower severity than at baseline). At the next visit one month later, patient had same psoriasis status as on previous visit. No adverse events observed. | Yes |
| F B | M | Nov. 30, 1930 | 69 | Psoriatic arthritis | 5 years | Mild to moderate Psoriasis on wrists, elbows, scalp, gluteous, right thigh. After 1 month treatment with Diacerein, Psoriasis severity improved from | Yes |

TABLE 1-continued

SUMMARY DATA

| Patient initials | Sex | Date of birth | Age (years) | Diagnosis | Duration of psoriasis | Results | Responder |
|---|---|---|---|---|---|---|---|
| | | | | | | moderate to mild. After a further month of treatment, Psoriasis severity was judged to be mild. No adverse events were reported. | |
| O B | M | Nov. 19, 1949 | 50 | Psoriatic arthritis | 5 years | At baseline, psoriasis was moderate on scalp. After 1 month of treatment with Diacerein, Psoriasis severity improved from moderate to slight. Patient stopped Diacerein treatment because of diarrhea. However patient showed improvement in psoriasis and arthritis in one month | Yes |
| A A | M | Feb. 3, 1925 | 75 | Psoriatic arthritis | 6 months | At baseline, psoriasis on scalp (20%). Area affected. Moderate erythema and infiltration, mild desquamation. Inguinal area and anal region also affected with moderate erythema and infiltration, desquamation. Patient reported that he had stopped Diacerein treatment after 4 weeks because his symptoms had disappeared. However, his psoriasis returned 3 weeks later in a mild form in the same areas as mentioned above. Doctor re-proposed Diacerein treatment. | Yes |
| I B | M | Feb. 5, 1935 | 65 | Psoriatic arthritis | 12 years | At baseline, Psoriasis severity was mild to moderate on scalp, right gluteous, and anterior region of both legs. After 1 month of treatment with Diacerein, the severity decreased. After another month of treatment, no or desquamation observed. Only mild infiltration present observed in affected areas. | Yes |
| A L | M | Jan. 7, 1927 | 73 | Psoriatic arthritis | 52 years | At baseline Psoriasis was mild to moderate on scalp, elbows and knees. Hands showed onychopathy. Scalp: 10% area affected. Moderate erythema and infiltration, mild desquamation Elbows: <30% area affected. Moderate erythema and infiltration, desquamation Knees: <30% area affected. Moderate erythema and infiltration, desquamation. After 1 month treatment with Diacerein, psoriasis status was unchanged. No adverse events observed. | No as treatment period was only 1 month |
| I M | F | Jun. 20, 1929 | 70 | Psoriatic arthritis | 10 years | At baseline psoriasis severity was mild to moderate on scalp, right thigh and sacral area. Scalp: 10% area affected. | Baseline visit only |

TABLE 1-continued

SUMMARY DATA

| Patient initials | Sex | Date of birth | Age (years) | Diagnosis | Duration of psoriasis | Results | Responder |
|---|---|---|---|---|---|---|---|
| | | | | | | Moderate erythema and infiltration, mild desquamation | |
| | | | | | | Right thigh: 10% area affected. Moderate erythema and infiltration, mild desquamation | |
| | | | | | | Sacral area: Moderate erythema and infiltration, desquamation | |
| A B | F | Aug. 6, 1947 | 53 | Psoriatic arthritis | 2 years | At baseline, patient presented psoriatic onychopathy. | |
| S I | M | Oct. 26, 1970 | 29 | Psoriatic arthritis | 6 years | At baseline patient had moderate psoriasis on scalp. | |

TABLE 2

INDIVIDUAL DATA

| Patient initials | Date of birth | Age (years) | Findings |
|---|---|---|---|
| M P (male) | May, 24 1952 | 47 | Diagnosis: Moderate PsA:<br>1$^{st}$ visit March 2000. Patient had psoriasis on scalp, elbows and right knee since June 2000.<br>AH 20%:   EH 2:   IH:2   DH:2<br>AU 30%;   EU 2:   IU:2   DU:2<br>AL 20%;   EL 2:   IL:2   DL:2<br>PASI score = 9.6<br>Arthritis: several joints (since Dec. 1999) with swelling. Pain on the VAS = 60 mm<br>2$^{nd}$ visit Jun. 6, 2000: Psoriasis decreased significantly in extent and severity.<br>Scalp:<br><br>AH 10%;<br>(Anterior)   EH 1:   IH:1   DH:1<br>(Posterior)   EH 2:   IH:2   DH:2<br>Elbows:<br><br>(Left sup.ext)   EU 1:   IU:1   DU:1<br>(Right + left ext pleats)   EU 2:   IU:2   DU:2<br>Right knee   EL 1:   IL:1   DL:1<br>PASI score = 6.6<br>Pain and swelling in the joints did not show much improvement. Pain on the VAS = 50 mm.<br>3$^{rd}$ visit Jul. 3, 2000: Psoriasis improved further. Slight erythema and moderate desquamation observed on posterior part of scalp. It improved on the knee and left elbow.<br>Scalp<br><br>(Anterior)   EH 0:   IH:0   DH:0<br>(Posterior)   EH 2:   IH:2   DH:2<br>Elbows:<br><br>(Left sup.ext)   EU 0:   IU:1   DU:0<br>(Right + left ext. pleats)   EU 2:   IU:2   DU:2<br>Right knee   EL 0:   IL:1   DL:0<br>PASI = score 5.0<br>Joint swelling decreased in all joints. Pain on the VAS = 40 mm.<br>4$^{th}$ visit Aug. 18, 2000: Posterior part of the scalp showed slight erythema and desquamation. Left elbow showed only slight infiltration.<br>Scalp<br><br>(Anterior)   EH 0:   IH:0   DH:0<br>(Posterior)   EH 1:   IH:1   DH:1 |

TABLE 2-continued

INDIVIDUAL DATA

| Patient initials | Date of birth | Age (years) | Findings |
|---|---|---|---|
| | | | Elbow: |
| | | | (Left)  EU 0:  IU:1  DU:0 |
| | | | PASI score = 0.9 |
| | | | For arthropathy, only occasional pain at MTF joint |
| E M (male) | Feb. 26, 1959 | 42 | Diagnosis: Mild to moderate PsA. |
| | | | First visit: Apr. 17, 2000. |
| | | | Psoriasis (since 1979). Lower limbs, right gluteus, elbows and scalp affected. |
| | | | AH <10%;  EH 1:  IH:1  DH:1 |
| | | | AU 30%;   EU 2:  IU:2  DU:1 |
| | | | AL 30%;   EL 1:  IL:2  DL:1 |
| | | | PASI score = 8.1 |
| | | | Arthritis: right knee with swelling (Ritchie 3) and pain on the VAS = 50 mm. |
| | | | $2^{nd}$ visit Jun. 0, 2000: After 2 months treatment, the psoriasis disappeared in June. |
| | | | $3^{rd}$ visit: Jul. 19, 2000: Psoriasis reappeared on the lower limbs and scalp (with a lower severity than at baseline). |
| | | | AH 10%:   EH 1:  IH:1  DH:1 |
| | | | AL 30%;   EL 1:  IL:1  DL:1 |
| | | | PASI score = 3.9 |
| | | | Arthritis: right knee with swelling (Ritchie 3) and pain on the VAS = 50 mm. |
| | | | $4^{th}$ visit Aug. 29, 2000: Psoriasis status as on Jul. 19, 2000. Right knee was not swollen (Ritchie 0) and had no pain (VAS = 1 cm) |
| F B (male) | Nov. 30, 1930 | 69 | Diagnosis = psoriatic arthritis |
| | | | First visit: Jun. 22, 2000. Psoriasis: Since 1995. Mild to moderate on wrists, elbows, scalp, gluteous, right thigh. |
| | | | AH <10%;  EH 2:  IH:2  DH:1 |
| | | | AU <30%;  EU 2:  IU:2  DU:2 |
| | | | AL <30%;  EL 2:  IL:2  DL:1 |
| | | | PASI score = 6.9 |
| | | | Arthritis: since December 1999. Right and left wrists. (Ritchie 2). Extension of toes of right foot (swollen). |
| | | | Pain on VAS = 80 mm. |
| | | | $2^{nd}$ visit: Jul. 20, 2000 |
| | | | Psoriasis severity improved from moderate to slight. |
| | | | EH 1:  IH:2  DH:1 |
| | | | EU 1:  IU:1  DU:1 |
| | | | EL 1:  IL:1  DL:1 |
| | | | PASI score = 6.9 |
| | | | Arthritis: Swelling of toes of right foot disappeared. |
| | | | Wrist dx: improved from Ritchie 2 to 1. |
| | | | Wrist sx: improved from Ritchie 2 to 0 |
| | | | Slight pain in IFP joint |
| | | | $3^{rd}$ visit: Aug. 24, 2000 |
| | | | Psoriasis severity improved to mild. |
| | | | EH 1:  IH:1  DH:1 |
| | | | EU 1:  IU:1  DU:1 |
| | | | EL 1:  IL:1  DL:1 |
| | | | PASI score = 3.9 |
| | | | Arthritis: Wrist dx: improved from Ritchie 1 to 0. |
| | | | Wrist sx: Ritchie 0 |
| | | | Pain in IFP joint disappeared |
| | | | Morning stiffness = 30 minutes. |
| O B (male) | Nov. 19, 1949 | 50 | Diagnosis = psoriatic arthritis |
| | | | First visit: Jun. 16, 2000. Psoriasis: Since 1995. Moderate on scalp. |
| | | | AH 10%;   EH 2:  IH:2  DH:2 |
| | | | PASI score = 0.6 |
| | | | Arthritis: $2^{nd}$ MCF, dx, Ritchie 2. |
| | | | Pain on VAS = 20 mm |
| | | | $2^{nd}$ visit: Jul. 20, 2000 |
| | | | Psoriasis severity improved from moderate to slight. |
| | | | AH 10%;   EH 1:  IH:1  DH:1 |
| | | | PASI score = 0.1 |
| | | | Arthritis: $2^{nd}$ MCF, dx, improved from Ritchie 1 to Ritchie 0. |
| | | | Patient stopped Diacerein treatment because of diarrhea. |
| | | | However patient showed improvement in psoriasis and arthritis in one month |
| A A (male) | Feb. 3, 1925 | 75 | Diagnosis = psoriatic arthritis |
| | | | First visit: Jun. 8, 2000. Psoriasis: Since January 2000. |
| | | | The scalp, area under the chin, inguinal area and anal region affected. |

TABLE 2-continued

INDIVIDUAL DATA

| Patient initials | Date of birth | Age (years) | Findings |
|---|---|---|---|
| | | | Scalp:<br>AH 20%; EH 2: IH:2 DH:2<br>Area under the chin:<br>EU 2: IU:2 DU:2<br>Inguinal area and anal region:<br>EL 2: IL:2 DL:2<br>PASI score = 4.8<br>Arthritis:<br>TMC sx (Ritchie 1)<br>Tibiotarsal joint sx (Ritchie 2) swollen.<br>Shoulder sx (Ritchie 1)<br>Pain on VAS = 40 mm<br>2$^{nd}$ visit: Aug. 18, 2000.<br>Patient reported that he had stopped Diacerein treatment in mid-July because his symptoms had disappeared.<br>Later his psoriasis returned in a mild form in the same areas as mentioned above.<br>Psoriasis: E1 I1 D1<br>PASI score = 2.4<br>Arthritis:<br>TMC sx improved from Ritchie 1 to 0<br>Tibiotarsal joint sx: improved from Ritchie 2 to 0.<br>Shoulder sx: improved from Ritchie 1 to 0<br>Doctor proposed Diacerein treatment again. |
| I B (M) | Feb. 5, 1935 | 65 | Diagnosis = psoriatic arthritis<br>First visit: Jun. 8, 2000. Psoriasis: Since 1988.<br>Scalp:<br>AH 10%; EH 2: IH:2 DH:2<br>Right gluteous:<br>A 30%; E 2: I:2 D:2<br>Legs bilateral anterior region:<br>AL 30%; EL 2: IL:2 DL:2<br>PASI score = 13.6<br>Arthritis: since 1982<br>Shoulder sx: Ritchie 1<br>Hip sx: Ritchie 2<br>TMC dx: Ritchie 1<br>Pain on VAS = 50 mm<br>2$^{nd}$ visit: Jul. 13, 2000.<br>Psoriasis: The severity of the psoriasis improved after one month of treatment<br>Scalp:<br>AH 10%; EH 1: IH:2 DH:1<br>Right gluteous:<br>A 30%; E 1: I:1 D:1<br>Legs bilateral anterior region:<br>AL 30%; EL 1: IL:1 DL:1<br>PASI score = 6.7<br>Arthritis:<br>Shoulder sx: Unchanged<br>Hip sx: Unchanged<br>TMC dx: Improved from Ritchie 1 to 0<br>Pain on VAS = 50 mm.<br>3$^{rd}$ visit: Aug. 30, 2000.<br>Psoriasis: Psoriatic status improved significantly after 2 months treatment. No erythema or desquamation observed in the affected regions. Only mild infiltration present<br>Scalp:<br>EH 0: IH:1 DH:0<br>Right gluteous:<br>E 0: I 1 D 0<br>Legs bilateral anterior region:<br>EL 0: IL:1 DL:0<br>PASI score = 2.2<br>Arthritis:<br>Shoulder sx: Unchanged<br>Hip sx: Unchanged<br>TMC dx: Improved from Ritchie 1 to 0<br>Pain on VAS = 50 mm. |
| A L (male) | Jan. 17, 1927 | 73 | Diagnosis = psoriatic arthritis<br>First visit: Jun. 12, 2000.<br>Psoriasis: Since 1948.<br>Hands: Onychopathy<br>Scalp |

TABLE 2-continued

INDIVIDUAL DATA

| Patient initials | Date of birth | Age (years) | Findings |
|---|---|---|---|
| | | | AH 10%; EH 2: IH:2 DH:1 |
| | | | Elbows |
| | | | AU <30%; EU 2: IU:2 DU:2 |
| | | | Knees |
| | | | AL 30%; EL 2: IL:2 DL:2 |
| | | | PASI score = 10.1 |
| | | | Arthritis: Since February 2000. |
| | | | Bilateral knee pain (Ritchie 1) |
| | | | Tibiotarsal joint dx (Ritchie 2). |
| | | | Pain on VAS = 60 mm |
| | | | $2^{nd}$ visit: Jul. 14, 2000 |
| | | | Psoriasis: status unchanged. |
| | | | Arthritis: No joint pain until 2 days before second visit. Then had knee pain (bilateral) (Ritchie 1). |
| | | | Pain on VAS = 50 mm |
| I M (F) | June 20, 1929 | 70 | Diagnosis = psoriatic arthritis |
| | | | First visit: Jun. 7, 2000. Psoriasis: Since 1990. |
| | | | Scalp: |
| | | | AH 10%; EH 2: IH:2 DH:2 |
| | | | Right thigh: |
| | | | A 10%; EU 2: IU:2 DU:2 |
| | | | Sacral area: |
| | | | E 2: I 2 D 2 |
| | | | PASI score = 4.8 |
| | | | Arthritis: since 1990 |
| | | | Cervical spine: Ritchie 2 |
| | | | IFP $3^{rd}$ finger dx hand (Ritchie 2) slightly swollen. |
| | | | I and II MCF sx hand (Ritchie 1) sub-bursal |
| | | | Pain on VAS = 50 mm |
| A B (female) | Aug. 6, 1947 | 53 | Diagnosis = psoriatic arthritis |
| | | | First visit: Aug. 31, 2000. Psoriatic onychopathy: hands since 1998 |
| | | | Arthritis: since 1995. Right wrist, left and right hand, |
| | | | Right tibia-tarsal joint all tender and very painful (Ritchie 2–3) |
| | | | Pain on VAS = 70 mm. |
| S I (male): | Oct. 26, 1970 | 29 | Diagnosis = psoriatic arthritis. |
| | | | First visit: Aug. 28, 2000. Psoriasis since 1994. |
| | | | Scalp: |
| | | | AH 20%; EH 2: IH:2 DH:2 |
| | | | PASI score = 1.2 |
| | | | Arthropathy: (since 1996) |
| | | | IFP of hands (Ritchie 1) |
| | | | Right shoulder (Ritchie 1) |
| | | | Tendinitis of the right foot (medially) |
| | | | Pain = 50 mm on VAS |
| | | | Morning stiffness = 90 minutes |

Conclusions

Of the seven patients (including the drop-out patient) who took Diacerein for one month or more, all (100%) had responded to treatment.

The only adverse effect reported was diarrhea in one patient, which caused the patient to drop-out of the study.

Considering the above results, diacerein has surprisingly shown to be effective in the treatment of psoriasis and associated diseases.

What is claimed is:

1. A method for treating psoriasis comprising administering to a human being suffering from psoriasis a therapeutically effective amount of a pharmaceutical composition comprising diacerein or a pharmaceutically acceptable salt or ester thereof.

2. The method of claim 1, wherein the pharmaceutical composition is administered topically in a form of a cream or ointment on portions of the human affected by psoriasis.

3. The method according to claim 1, wherein said pharmaceutical composition is in a form adapted for oral administration.

4. A method for treating psoriasis comprising administering to a human being suffering from psoriasis a pharmaceutical composition comprising a therapeutically effective amount of diacerein.

5. The method of claim 4, wherein the pharmaceutical composition is administered topically in a form of a cream or ointment on portions of the human affected by psoriasis.

6. The method of claim 4, wherein said pharmaceutical composition is in a form adapted for oral administration.

7. The method of claim 6, wherein the pharmaceutical composition is administered at a daily oral administration dosage of 30–200 mg of diacerein.

8. The method of claim 6, wherein the pharmaceutical composition is administered at a dosage of 100 mg daily of diacerein, in at least two administrations.

9. The method of claim 1, wherein said pharmaceutical composition comprises a therapeutically effective amount of diacerein.

10. A method for treating psoriasis comprising administering to a human being suffering from psoriasis a therapeutically effective amount of diacerein.

* * * * *